US009968564B2

(12) United States Patent
Gaonkar et al.

(10) Patent No.: US 9,968,564 B2
(45) Date of Patent: May 15, 2018

(54) DELIVERY OF FUNCTIONAL COMPOUNDS

(75) Inventors: Anilkumar Ganapati Gaonkar, Buffalo Grove, IL (US); Ahmad Akashe, Mundelein, IL (US); Les Lawrence, Rolling Meadows, IL (US); Amado R. Lopez, Chicago, IL (US); Ronald L. Meibach, Deerfield, IL (US); Dana Sebesta, Plano, IL (US); James D. White, Hanover Park, IL (US); Yan Wang, Glenview, IL (US); Leslie G. West, Winnetka, IL (US)

(73) Assignee: Intercontinental Great Brands LLC, East Hanover, NJ (US)

( * ) Notice: Subject to any disclaimer, the term of this patent is extended or adjusted under 35 U.S.C. 154(b) by 575 days.

(21) Appl. No.: 12/479,444

(22) Filed: Jun. 5, 2009

(65) Prior Publication Data

US 2010/0310666 A1    Dec. 9, 2010

(51) Int. Cl.
    *A61K 31/00*      (2006.01)
    *A61K 31/015*    (2006.01)
    *A23P 10/30*     (2016.01)
    *A23L 33/105*    (2016.01)

(52) U.S. Cl.
    CPC ............ *A61K 31/00* (2013.01); *A23L 33/105* (2016.08); *A23P 10/30* (2016.08); *A61K 31/015* (2013.01)

(58) Field of Classification Search
None
See application file for complete search history.

(56) References Cited

U.S. PATENT DOCUMENTS

| | | | |
|---|---|---|---|
| 2,464,204 A | 3/1949 | Baker | |
| 2,727,833 A | 12/1955 | Yen et al. | |
| 3,010,953 A | 11/1961 | Unger et al. | |
| 3,041,289 A | 6/1962 | Katchen et al. | |
| 3,116,206 A | 12/1963 | Brynko et al. | |
| 3,869,406 A | 3/1975 | Matsukawa et al. | |
| 3,956,172 A | 5/1976 | Saeki et al. | |
| 4,518,458 A | 5/1985 | Greenfield et al. | |
| 4,601,863 A | 7/1986 | Shioi et al. | |
| 4,687,667 A * | 8/1987 | Rhodes et al. | 424/745 |
| 4,702,798 A | 10/1987 | Bonanno | |
| 4,778,781 A | 10/1988 | Washizu et al. | |
| 4,895,725 A | 1/1990 | Kantor et al. | |
| 4,936,916 A | 6/1990 | Shinmitsu et al. | |
| 5,051,304 A | 9/1991 | David et al. | |
| 5,051,305 A | 9/1991 | Whitaker, Sr. | |
| 5,146,758 A | 9/1992 | Herman | |
| 5,160,742 A * | 11/1992 | Mazer et al. | 424/469 |
| 5,164,210 A * | 11/1992 | Campbell et al. | 426/5 |
| 5,418,010 A * | 5/1995 | Janda et al. | 427/213.31 |
| 5,480,656 A | 1/1996 | Okada et al. | |
| 5,601,760 A | 2/1997 | Rosenberg | |
| 5,679,377 A | 10/1997 | Bernstein et al. | |
| 5,686,092 A | 11/1997 | Lewis | |
| 5,879,541 A | 3/1999 | Parkinson | |
| 5,958,388 A | 9/1999 | Franks | |
| 6,143,170 A | 11/2000 | Briggs et al. | |
| 6,608,017 B1 | 8/2003 | Dihora et al. | |
| 6,653,288 B1 | 11/2003 | Beuvry et al. | |
| 6,770,285 B2 | 8/2004 | Keenan et al. | |
| 6,921,539 B2 | 7/2005 | Ninkov | |
| 6,923,988 B2 | 8/2005 | Patel et al. | |
| 6,929,810 B2 | 8/2005 | Purohit et al. | |
| 6,929,814 B2 | 8/2005 | Bouwmeesters et al. | |
| 7,067,153 B2 | 6/2006 | Grisoni | |
| 7,182,959 B2 | 2/2007 | Martani | |
| 7,192,542 B2 | 3/2007 | Ugazio | |
| 7,250,185 B2 | 7/2007 | Dowdle et al. | |
| 7,279,495 B2 | 10/2007 | Ducray et al. | |
| 7,338,928 B2 | 3/2008 | Lau et al. | |
| 7,427,407 B2 | 9/2008 | Kume et al. | |
| 7,541,155 B2 | 6/2009 | Enan | |
| 7,585,538 B2 | 9/2009 | Mangos et al. | |
| 7,622,269 B2 | 11/2009 | Enan | |
| 2002/0055537 A1 | 5/2002 | Gerlach et al. | |
| 2002/0173522 A1 | 11/2002 | Redmon et al. | |
| 2002/0193452 A1 | 12/2002 | Brocker et al. | |
| 2003/0082272 A1 * | 5/2003 | Bouwmeesters et al. | 426/5 |
| 2003/0175403 A1 | 9/2003 | Gurin | |

(Continued)

FOREIGN PATENT DOCUMENTS

| | | |
|---|---|---|
| AU | 614943 B | 9/1991 |
| EP | 0 351 760 A2 | 1/1990 |

(Continued)

OTHER PUBLICATIONS

Salgueiro et al. Chemical Composition and Antifungal Activity of the Essentail Oil of Orignaum virens on *Candida* Species, Plant Med 2003 69: 871-874.*

Muttil et al. Inhalable Microparticles Containing Large Payload of Anti-tuberculosis Drugs, European Journal of Pharmacetucial Sciences 32 (2007) 140-150.*

Agnihotri et al. Recent Advnaces in Chitosan-Based Micro- and Nanoparticles in Drug Delivery, Journal of Controlled Release 100 (2004) 5-28.*

Leopold et al. In virto study for the assessment of poly(L-aspartic acid) as a drug carrier for colon-specific drug delivery, International Journal of Pharmaceutics 126 (1995) 139-145 (1995).*

(Continued)

*Primary Examiner* — David J Blanchard
*Assistant Examiner* — Alissa Prosser
(74) *Attorney, Agent, or Firm* — Fitch, Even, Tabin & Flannery, LLP

(57) ABSTRACT

Functional ingredients including an esterified component and microencapsulated in an enteric matrix to increase the microencapsulation efficiency and reduce undesired organoleptic properties of the microencapsulated material while providing a desired release rate and ester hydrolysis rate, the process including forming an emulsion in water and titrating the emulsion with a precipitating agent to produce a particulate precipitate.

18 Claims, 6 Drawing Sheets

(56) References Cited

U.S. PATENT DOCUMENTS

| | | |
|---|---|---|
| 2003/0180369 A1 | 9/2003 | Grisoni |
| 2003/0203848 A1 | 10/2003 | Vertesy et al. |
| 2003/0225003 A1 | 12/2003 | Ninkov |
| 2003/0228369 A1 | 12/2003 | Kuhrts |
| 2004/0109894 A1 | 6/2004 | Shefer et al. |
| 2004/0191366 A1 | 9/2004 | Mangos et al. |
| 2004/0195711 A1 | 10/2004 | Hayashi et al. |
| 2004/0266888 A1 | 12/2004 | Ninkov |
| 2005/0014827 A1 | 1/2005 | Schur |
| 2005/0054682 A1 | 3/2005 | Phillips |
| 2005/0079138 A1 | 4/2005 | Chickering, III et al. |
| 2005/0100640 A1 | 5/2005 | Pearce |
| 2005/0123603 A1 | 6/2005 | Dalland et al. |
| 2005/0181059 A1 | 8/2005 | Jacob et al. |
| 2005/0200035 A1 | 9/2005 | Dobbs |
| 2005/0287276 A1 | 12/2005 | Lavoie et al. |
| 2006/0134282 A1 | 6/2006 | Mellema |
| 2006/0147503 A1 | 7/2006 | Floyd |
| 2006/0280795 A1 | 12/2006 | Penhasi et al. |
| 2007/0072944 A1 | 3/2007 | Gauvry et al. |
| 2007/0134332 A1 | 6/2007 | Turnell et al. |
| 2007/0141147 A1 | 6/2007 | Heil et al. |
| 2007/0145326 A1 | 6/2007 | Joseph et al. |
| 2007/0148198 A1 | 6/2007 | Joseph et al. |
| 2007/0190080 A1 | 8/2007 | Friedman |
| 2007/0218125 A1 | 9/2007 | Head et al. |
| 2008/0020078 A1 | 1/2008 | Enan |
| 2008/0029625 A1 | 2/2008 | Talton |
| 2008/0038362 A1 | 2/2008 | Park et al. |
| 2008/0125461 A1 | 5/2008 | Barberich |
| 2008/0145462 A1 | 6/2008 | Enan |
| 2008/0193531 A1 | 8/2008 | Hermelin et al. |
| 2008/0207766 A1 | 8/2008 | Devane |
| 2008/0226623 A1 | 9/2008 | Margolin et al. |
| 2008/0226649 A1 | 9/2008 | Schetter et al. |
| 2008/0226684 A1 | 9/2008 | Peppas |
| 2008/0255498 A1 | 10/2008 | Houle |
| 2008/0260819 A1 | 10/2008 | Fleming et al. |
| 2008/0299087 A1 | 12/2008 | Tseng et al. |
| 2009/0186096 A1 | 7/2009 | Kritzman et al. |
| 2010/0310726 A1 | 12/2010 | Akashe et al. |
| 2011/0008471 A1 | 1/2011 | Enan |
| 2011/0020520 A1 | 1/2011 | Van Lengerich et al. |
| 2011/0124502 A1 | 5/2011 | Enan |
| 2012/0251641 A1 | 10/2012 | Enan et al. |

FOREIGN PATENT DOCUMENTS

| | | | |
|---|---|---|---|
| EP | 579435 | | 1/1994 |
| EP | 0 610 957 A2 | | 8/1994 |
| EP | 0 827 997 A1 | | 3/1998 |
| EP | 1 396 551 A1 | | 3/2004 |
| EP | 1 721 605 A1 | | 11/2006 |
| GB | 2 005 537 A | | 4/1979 |
| JP | 52-152876 A | | 12/1977 |
| JP | S63-197540 A | | 8/1988 |
| JP | H02-103289 A | | 4/1990 |
| JP | 04-330934 A | | 11/1992 |
| JP | 05-017338 A | | 1/1993 |
| JP | 08-026930 A | | 1/1996 |
| JP | 10-273650 A | | 10/1998 |
| JP | 2003-012526 A | | 1/2003 |
| JP | 2004-018443 A | | 1/2004 |
| JP | 2007-177129 A | | 7/2007 |
| JP | 2008-013529 A | | 1/2008 |
| RU | 2 098 121 C1 | | 12/1997 |
| RU | 2 332 257 C2 | | 3/2006 |
| RU | 2 311 953 C2 | | 12/2007 |
| SU | 339029 | | 5/1972 |
| SU | 447163 A1 | | 10/1974 |
| WO | 82/02496 A1 | | 8/1982 |
| WO | 84/03201 A1 | | 8/1984 |
| WO | 93/19622 A1 | | 10/1993 |
| WO | 99/13869 A1 | | 3/1999 |
| WO | WO200036924 | * | 6/2000 ............ A23G 3/30 |
| WO | 02/38181 A2 | | 5/2002 |
| WO | 03/097015 A1 | | 11/2003 |
| WO | 2005/082320 A1 | | 9/2005 |
| WO | 2006093838 | | 9/2006 |
| WO | WO2007044437 A2 | * | 4/2007 ......... A61K 31/045 |
| WO | 2007/094009 A2 | | 8/2007 |
| WO | 2008/003996 A1 | | 1/2008 |
| WO | WO 2008/003007 | * | 1/2008 |
| WO | WO 2009/117623 | * | 9/2009 |

OTHER PUBLICATIONS

Kolhe et al. Preparation, Cellular transport, and Activity of Polyamidoamine-based Dendritic Nanodevices wtih a high drug Payload, Biomaterials 27 660-669 (2005).*
Raal et al. "Content and composition of the essential oil of Thymus serpyllum L. growing wild in Estonia," Medicina (Kaunas) 40(8):795-800, 2004.*
SIDS Initial Assessment Report dated Mar. 2002; http://www.chem.unep.ch/irptc/sids/OECDSIDS/115957.pdf.*
Wikipedia entry for lavender oil, 2013.*
Evans et al. "Quantitative structure-activity relationships and carminative activity" Journal of Pharmaceutical Sciences 67(2):277-278, 1972.*
Lis-Balchin et al. "Studies on the mode of action of the essential oil of lavender (Lavandula angustifolia P. Miller)" Phytotherapy Research 13:540-542, 1999.*
Ghelardini et al. "Local anaesthetic activity of the essential oil Lavandula angustifolia," Planta Medica 65:700-703, 1999.*
European Patent Office Extended European Search Report for European Application 10251044.3 dated Feb. 21, 2011 (6 pages).
C. L. Kruger and S.W. Mann, Safety evaluation of functional ingredients, Food and Chemical Toxicology, vol. 41, No. 6, Jan. 1, 2003, pp. 793-805, XP009144244, Pergamon, Great Britain.
Nicholas Parris et al., Encapsulation of Essential Oils in Zein Nanospherical Particles, Journal of Agricultural and Food Chemistry, vol. 53, Jun. 15, 2005, pp. 4788-4792, XP-002599360, American Chemical Society, United States of America.
M. A. Del Nobile et al., Antimicrobial efficacy and release kinetics of thymol from zein films, Journal of Food Engineering, vol. 89, No. 1, Nov. 1, 2008, pp. 57-63, XP022704837, Barking, Essex, Great Britain.
Intellectual Property Office of New Zealand Examination Report dated Jun. 2, 2010 for New Zealand Application 585724, 3 pages.
European Patent Office Extended European Search Report for European Application No. 10251026.0 dated Aug. 30, 2010 (7 pages).
Intellectual Property Office of New Zealand Examination Report dated Jun. 1, 2010 for New Zealand Application 585723, 3 pages.
Intellectual Property Office of New Zealand Examination Report dated Jun. 2, 2010 for New Zealand Application 585725, 3 pages.
PCT International Searching Authority International Search Report and Written Opinion for International Application No. PCT/US2011/065828 dated May 23, 2012, 11 pages.
Max S. Dunn and Howard B. Lewis, "The Action of Nitrous Acid on Casein," Journal of Biological Chemistry, vol. 49, 1921, pp. 327-341.
L. K. Ramachandran and W. B. McConnell, "The Action of Sulphuric Acid on Gliadin: With Special Reference to the N-Peptidyl→O-Peptidyl Bond Rearrangement," Canadian Journal of Chemistry, vol. 33, 1955, pp. 1638-1648.
R. M. Allison et al., "Notes on a deamination method proposed for determining 'chemically available lysine' of proteins," British Journal of Nutrition, vol. 29, 1973, pp. 51-55.
J. W. Paulis, "Disulfide Structures of Zein Proteins from Corn Endosperm," Cereal Chemistry, vol. 58, No. 6, 1981, pp. 542-546.
Microencapsulation of Food Ingredients, Edited by Per Vilstrup, Leatherhead Food RA Publishing, 2001, pp. 5-6.
LinShu Liu et al., "Pectin/Zein Beads for Potential Colon-Specific Drug Delivery: Synthesis and in Vitro Evaluation," 2006a, vol. 13, pp. 417-423.

* cited by examiner

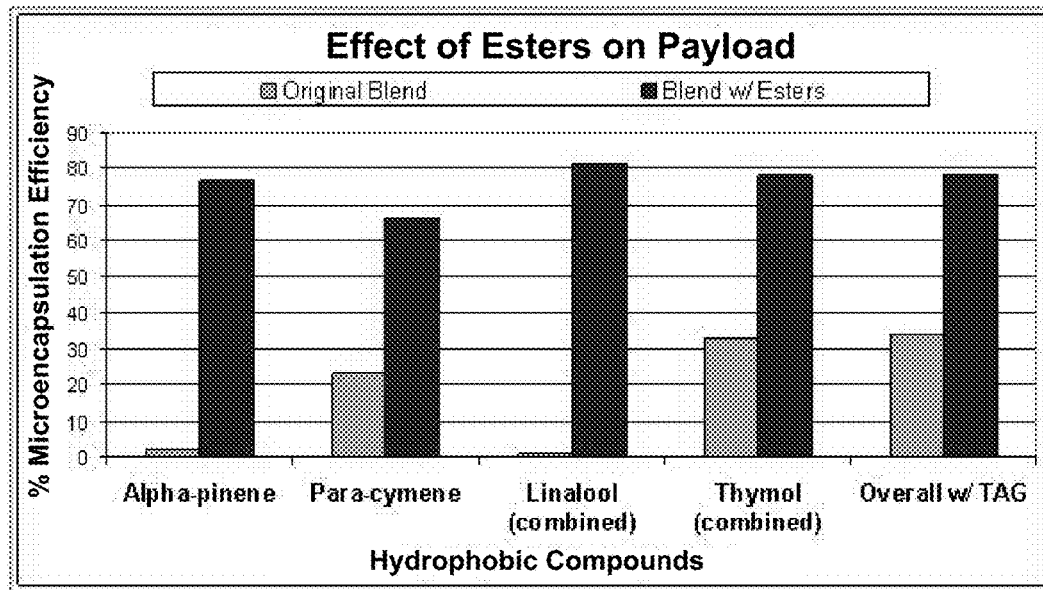

FIGURE 2

| Compound | Empirical Formula | Solubility in Water | Vapor Pressure (H2O=17torr@20C) | Partition coefficient (octanol / water) as log Kow | Affinity for oil as a ratio to water |
|---|---|---|---|---|---|
| a-pinene | C10H16 | insoluble | 3torr@20C | 4.83 | 67,000:1 |
| p-cymene | C10H14 | insoluble | 1.5torr@20C | 4.1 | 10,000:1 |
| linalool | C10H18O | .16g/100ml | 0.15torr@20C | 2.97 | 1,000:1 |
| linalyl acetate | C12H20O2 | .001g/100ml | 0.005torr@20C | 3.9 | 8000:1 |
| linalyl butyrate | C14H24O2 | insoluble | 0.009torr@20C | 4.9 | 79000:1 |
| thymol | C10H14O | .1g/100ml | 0.04torr@20C | 3.3 | 2,000:1 |
| thymyl acetate | C12H16O2 | .05g/100ml | 0.03torr@25C | 3.59 | 4,000:1 |

FIGURE 3

DELIVERY OF FUNCTIONAL COMPOUNDS

PARTIES TO A JOINT RESEARCH AGREEMENT

The claimed invention was made by a party, Kraft Foods Holdings, Inc., to a Joint Research Agreement. The Joint Research Agreement was executed and in effect on or before the date the claimed invention was made. The claimed invention was made as a result of activities undertaken within the scope of the Joint Research Agreement, and relates to the delivery of functional compounds. The parties to the Joint Research Agreement are TyraTech, LLC. and Kraft Foods Holdings, Inc. and Kraft Foods Global, Inc.

FIELD OF THE INVENTION

The present invention relates to an ester-containing functional ingredient which is microencapsulated by an enteric matrix and methods for making the same. More particularly, the functional ingredient is microencapsulated in an aqueous environment which is substantially free of organic solvents.

BACKGROUND OF THE INVENTION

Enteric delivery of functional materials in food delivery applications has been limited. Enteric delivery systems are commonly utilized when the functional materials or medicaments are known to be sensitive to low pH or have undesirable flavor and/or taste characteristics which cannot be effectively masked by other methods. Generally, enteric delivery is accomplished using tablets and gel capsules. However, those particular delivery methods are not well suited for food applications. In particular, neither tablets nor capsules are sized to be integrated into most existing food products.

An alternative process for enteric delivery is microencapsulation. Microencapsulation is generally performed using specialized equipment or in an environment including organic solvents. These methods require additional capital expenditures and the use of additional materials, such as the organic solvents, which may or may not be usable in subsequent microencapsulation cycles. As a result, the process of microencapsulation requires investments in both equipment and organic solvent procurement and disposal.

One issue with microencapsulation is the recovery rate, or microencapsulation efficiency of the process. Generally, a certain significant percentage of the material to be microencapsulated is not captured. The uncaptured material may be recovered for reuse, recycled, or a percentage of the uncaptured material remains adhered to the outer surface of the microencapsulated particulates.

As a result, the product tends to have a taste profile associated with the uncaptured material, which is often undesirable. This is particularly true when the uncaptured material includes oxidizable triglycerides such as unsaturated and polyunsaturated lipids, oxidizable flavors and essential oils, or other organic compounds that may naturally have undesirable taste and/or flavor.

SUMMARY OF THE INVENTION

The composition of the present invention includes a functional ingredient microencapsulated in an enteric matrix, such as described in U.S. patent application Ser. No. 12/479,454, filed the same day as this application, which is incorporated by reference in its entirety herein. The enteric matrix comprises a food grade polymer and the functional ingredient comprises esters of an essential oil, such as linalool and thymol.

In one embodiment, the functional ingredient is homogeneously dispersed throughout the enteric matrix material. In another embodiment, the functional ingredient comprises at least about 30% esters, such as esters of linalool and thymol.

The method of the present invention includes a method of microencapsulating an active or functional ingredient. The method includes agitating or mixing water, an enteric matrix material and an emulsifier to form a combination, at a pH that maintains complete dissolution of the enteric polymers being utilized, the combination being substantially free of organic solvents. A functional ingredient comprising esters is added to the combination and homogenized to create a fine, stable emulsion. The emulsion is then treated with an acid and/or other cross-linking or precipitating agents depending on the polymer being used, such as calcium, under controlled mixing conditions and in an amount and at a rate effective to form a particulate precipitate. Further, the functional ingredient is homogeneously dispersed throughout the precipitate and with an improved microencapsulation efficiency of the functional ingredient.

BRIEF DESCRIPTION OF THE DRAWINGS

FIG. 2 is a chart comparing the microencapsulation efficiency between two experiments, with one experiment including a functional ingredient that does not contain at least 30 percent esters, the second experiment including a functional ingredient that includes at least 30 percent esters of linalool and thymol;

FIG. 3 is a table showing the known empirical formula, solubility in water, vapor pressure, partition coefficient and a ratio comparing the affinity for oil to water ratio of various esters;

DETAILED DESCRIPTION OF THE PREFERRED EMBODIMENTS

Disclosed is the microencapsulation of an esterified functional ingredient and a non-active carrier(s) in an enteric matrix that minimizes release prior to dissolution in the intestine. Generally, including esterified functional ingredients solves issues encountered such as taste and/or flavor masking, enteric and sustained delivery, and retention of the functional ingredients at the proper ratios while ensuring bioavailability and efficacy.

In particular, the functional ingredient to be microencapsulated can include esterified forms of essential oils. When ingested and released in the intestinal tract, the esterified form of the functional ingredient is hydrolyzed into the parent, non-esterified form and provides the same functional benefits as if the non-esterified functional ingredient was microencapsulated and consumed. Further, the esterified forms of the functional ingredient provide additional benefits as will be discussed further below. In particular, the organoleptic properties of the esterified form include a higher taste threshold, which, as a result, esterified functional ingredients on the surface produce a less undesirable flavor profile. Further, esters are generally known to produce more desirable flavors, and therefore any flavors produced would not result in a wholly undesirable organoleptic flavor profile. Further, due to the low water solubility of the esterified functional ingredients, particularly in reference to the parent non-esterified functional ingredients, the below described method can result in a higher microencapsulation efficiency, as can be shown by a higher payload and retention rate, than has been recognized in the absence of esterified functional ingredients.

Examples of the use of the product created by the methods described herein are aimed at delivery in a powdered soft drink (PSD) beverage, however the product can be used in other food products, such as biscuits, bars, ice cream, snacks and instant meals.

Figure 1:
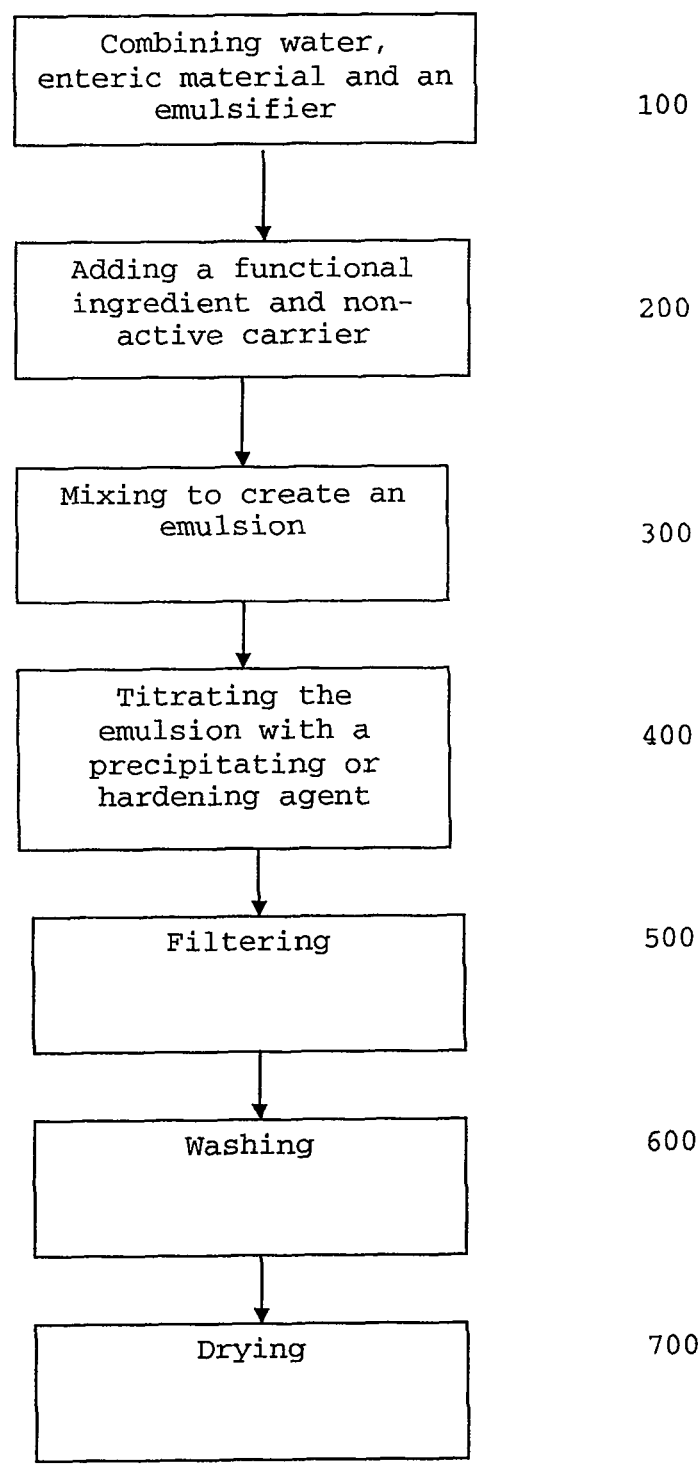
FIG. 1 illustrates a method for microencapsulating a functional ingredient.

A method for microencapsulating a functional ingredient is generally described in FIG. 1. Enteric delivery within a food matrix is achieved by the formation of matrix particles with the dispersed portion being that of the functional ingredient, such as an essential oil blend with diluent triglycerides, and the matrix portion is that of food grade enteric polymers, such as shellac, zein, calcium alginate, denatured whey protein and any and all food-grade enteric polymers known to practitioners of the art of microencapsulation alone or in combination.

As shown in FIG. 1, water, an enteric matrix material and an emulsifier are mixed or agitated until the enteric matrix material and emulsifier are fully dispersed in the water 100. Generally, the emulsifier and enteric matrix material can be added to the water together or separately, with either being added first. The pH is maintained at a level sufficient that allows for complete solubilization of the enteric material. As an example, for use of shellac, zein or combinations thereof the pH of the dispersion is generally between about 7.2 and 9.0. In some embodiments, a basic material, such as sodium, potassium or ammonium hydroxide, can be added to the dispersion to raise the pH, such as within a range from about 7.2 to about 12.0, preferably 8.0 to 11.3, to guarantee and maintain complete dissolution of the enteric polymers without the use of organic solvents.

As used herein, "agitation" or "agitated" refers to the use of a top entering mixer with impeller or a rotor/stator mixing device operating at a speed of less than 10,000 RPM.

As used herein, "substantially free of organic solvent" refers to an amount of added organic solvent, such as isopropanol or ethanol or any other organic solvent less than the amount required to enable solubility of the enteric material under the processing conditions. Preferably, the amount of added organic solvent is less than about 0.1 percent by weight of the combination of water, emulsifier and enteric material.

In one embodiment, the water is deionized water.

The enteric matrix material used herein is any food grade enteric polymer, or a combination of two or more food grade enteric polymers. Preferably, the enteric matrix material is shellac, zein, calcium alginate or combinations thereof. Other food grade enteric polymers include denatured whey protein. Preferably, the prepared enteric matrix material does not contain any organic solvents.

The emulsifier described herein may be any food grade emulsifier. In preferred embodiments, the emulsifier is polysorbate, polyglycerol ester, sucrose stearate, sucrose esters, proteins, lecithins or combinations thereof. More particularly, the emulsifier is preferably a sucrose ester due to the creation of the smaller and most uniformly dispersed oil droplets within the later created emulsion.

Generally, water comprises about 50.0 percent to about 95.0 percent of the dispersion by weight and preferably from about 70.0 to about 95.0 percent, and more preferably from about 80.0 to about 90.0 percent. The emulsifier generally comprises less than about 5.0 percent of the dispersion by weight, preferably from about 0.01 to about 1.0 percent by weight, and more preferably about 0.01 to about 0.1 percent by weight of the dispersion. Preferably, the enteric matrix material ranges from about 1.0 percent to about 10.0 percent by weight, preferably from about 4.0 to about 7.0 percent, and more preferably from about 5.0 percent to 6.0 percent by weight of the dispersion.

Upon forming the dispersion, a functional ingredient and a non-active carrier is added 200 and agitated 300 to provide a coarse emulsion having a droplet size of more than about 10 micrometers. After the coarse emulsion is formed, the coarse emulsion is homogenized 300 to create a fine, stable emulsion. The fine, stable emulsion has a droplet size of less than about 10 micrometers. Within the fine emulsion, the functional ingredient and non-active carrier are homogeneously dispersed in the form of fine droplets throughout. Preferably, the combination of the functional ingredient and non-active carrier is added in amount ranging from about 2.0 to about 7.0 percent of the emulsion by weight. More preferably, the combination of the functional ingredient and non-active carrier is added in an amount ranging from about 3.0 to about 6.0 percent of the emulsion by weight. The emulsion includes from about 60.0 to about 95.0 percent water.

As used herein, "homogenization" or "homogenized" refers to mixing at a speed greater than 10,000 RPM, such as the use of a rotor/stator mixing device or at a lower mixing speed of an elevated pressure, such as a valve homogenizer operating at a pressure of 500-10,000 psi.

The functional ingredient preferably includes esters of essential oils. As an example, the functional ingredient includes esters of thymol and linalool, such as thymyl and linalyl acetate. Other acceptable esters can be used, such as butyrates, lactates, cinnamates and pyruvates. In particular, the functional ingredient includes alpha-pinene, para-cymene, thymyl esters and linalyl esters. As discussed in the examples below, one exemplary blend includes, by weight, about 18.8 percent canola oil, about 8.6 percent alpha-pinene, about 39.8 percent para-cymene, about 5.4 percent linalool acetate and about 27.4 percent thymyl acetate.

The esters comprise from about 1.0 to about 99.0 percent of the functional ingredient by weight. Preferably, the esters comprise from at least about 10.0 percent of the functional ingredient by weight, more preferably 30 percent by weight. In another embodiment, preferably, the esters comprise from about 25.0 to about 65.0 percent of the functional ingredient by weight.

In a preferable embodiment, the blend of non-active carrier and functional ingredient includes, by weight, about 15.0 to about 30.0 percent canola oil, about 1.0 to about 10.0 percent alpha-pinene, about 5.0 to about 25.0 percent para-cymene, about 5.0 to about 20.0 percent linalyl ester and about 20.0 to about 60.0 percent thymyl ester. More preferably, the blend of non-active carrier and functional ingredient includes, by weight, about 20.0 to about 25.0 percent canola oil, about 2.0 to about 7.0 percent alpha-pinene, about 10.0 to about 20.0 percent para-cymene, about 7.0 to about 15.0 percent linalyl ester and about 35.0 to about 50.0 percent thymyl ester.

Generally, any esterified form of a functional ingredient, such as thymol and linalool, can be used. Preferably, the esterified form is an acetate or butyrate. More preferably, the esterified form is an acetate due to the increased rate of hydrolysis as compared to butyrate.

The functional ingredient can comprise a mixture of any essential oils. Further, the functional ingredient can be selected to include materials which are desired to be released enterically. As an example, the functional ingredient can include compositions described in U.S. Patent Publication No. 2008/0145462 to Enan. For example, they functional ingredient includes 25-35% by weight para-cymene, 1-10% by weight linalool, 1-10% by weight alpha-pinene, 35-45% by weight thymol, and 20-30% by weight soybean oil.

In particular, the functional ingredient described herein can include compounds which possess functional properties, such as anti-parasitic, anti-protozoan, and anti-fungal. In a preferred embodiment, the organic compounds further include alpha-pinene and para-cymene.

In one preferred embodiment, organic compounds are blended with a non-active carrier such as a lipid, fatty acid, triglyceride or food grade oil, such as soybean oil or canola oil.

The volatile nature of some of the functional ingredients leads to a very low threshold value for olfactory perception, resulting in an undesirable flavor/taste in the existing beverage/food. In an effort to mask the flavor of the functional ingredients, the invention calls for the inclusion of the far less water soluble esterified forms of the functional ingredient, such as thymol and linalool, as well as processes to remove unencapsulated material from the final ingredient. Esters generally have a less negative impact on the taste/flavor of the food system than their respective parent compounds.

Due to the low water solubility, an ester can have a higher microencapsulation efficiency, such as described above, than non-esterified parent compounds, such as thymol and linalool. Preferably, the efficiency increases about 50 to about 200 percent over the efficiency observed when using non-esterified functional ingredients, more preferably about 100.0 to about 150.0 percent. Further, esters have a higher olfactory perception threshold than the parent compounds, such that amount of esters necessary to be perceived is more than the amount of non-esterified thymol and linalool.

The emulsion is then precipitated by titration with an acid or with a cross-linking or precipitating agent 400. During precipitation, the emulsion can be subjected to agitation. In one embodiment, the emulsion is titrated with a solution 1-5 percent calcium chloride and 1-5 percent citric acid. In another embodiment, the emulsion is titrated with acid in an amount effective to decrease the pH below the isoelectric point, such as a pH of about 7.0, causing phase separation and inducing precipitation of the enteric matrix out of solution with the hydrophobic functional ingredient being microencapsulated therein, thus creating a slurry of an aqueous solution and precipitate. The precipitated slurry has a particle size from about 1.0 to about 1000.0 micrometers, preferably about 10.0 to about 500.0 micrometers, and more preferably from about 75.0 to about 250.0 micrometers.

More preferably, precipitation occurs at a pH ranging from about 3.0 to about 6.0, or further between a pH ranging from about 3.8 to about 4.6.

While not wishing to be limited by theory, it is believed that as the pH of the emulsion drops below the isoelectric point, the particles of enteric material, such as shellac and zein, may cross-link to like particles or to one another to form a matrix, the functional ingredient and non-active carrier being microencapsulated within the matrix. As a result, of the cross-linking, the functional ingredient is homogenously dispersed throughout the matrix. The matrix further provides a seal for the functional ingredient. As a result, the impact of the functional ingredient on the organoleptic qualities of the finished powder is correlated to any functional ingredient remaining adhered to the outer surface of the enteric matrix.

The acid used can include any food grade acid. In one embodiment, the acid is citric acid.

As noted above, the composition of the enteric matrix material affects the dissolution rate and the protection provided by the enteric matrix.

To reclaim the precipitate, the slurry is filtered 500, washed 600 and dried 700. In one embodiment, the slurry is filtered, the resultant slurry cake is then washed and refiltered prior to drying.

In any and all microencapsulation processes, there will remain at least marginal surface or unencapsulated material. With the desire to mask compounds with low perception thresholds, the unencapsulated material must be reduced to levels below perception in the final product matrix and/or solution. Preferably, the functional ingredient on the outer surface particulate precipitate is less than about 1.0 percent by weight of the final product.

In a preferable embodiment, a surface oil remover is added to the slurry after filtering to aid in removing residual surface oil from the precipitate, as described in co-pending U.S. application Ser. No. 12/479,433, which is incorporated by reference in its entirety herein. Further, the surface oil remover can also be added prior to the refiltering step.

After the precipitate has been filtered and washed, the precipitate is dried to form a powder. Drying can be conducted such that the powder has a moisture content of less than about 10.0 percent, preferably to a moisture content of about 2.0 to about 6.0 percent, more preferably about 3.0 to about 5.0 percent.

Further, the powder can be pulverized using known methods to reduce the particle size of the powder precipitate, and then further dried to a moisture content of less than 5.0 percent by known methods, such as with a fluidized bed dryer. The resultant particles have a particle size ranging from about 1.0 to about 1000.0 micrometers, preferably from about 10.0 to about 500.0 micrometers, and more preferably from about 75.0 to about 250.0 micrometers.

When drying the powder, the temperature should be maintained between about 25 C to about 70 C, preferably about 35 C to about 65 C. During other processing steps, it is preferable to maintain the temperature between about 4 C to about 40 C, more preferably about 4 C to about 30 C, and further preferable from about 15 C to about 28 C.

As will be discussed further below, and as shown in FIG. 2, the inclusion of thymyl and linalyl esters also results in an increased payload in the final ingredient, such as from about 5.0 to about 50.0 percent, due to the decreased water solubility of the oil blend. Large volumes of water are used in all examples and esterification of thymol and linalool reduces leaching from the wet or dry forms of the particles by these rinses. The ability to limit losses during processing allows for control over the final ratio of functional compounds in the food system, as shown to be important in US Patent Application US20080145462A1, (Enan, E. et al.) Thymol is also crystalline at room temperature and the substitution of thymyl acetate, as an example, would allow for easier processing since all functional ingredients will be in liquid form in that formulation.

Example 1: The Evaluation and Selection of Emulsifiers

Various emulsifiers were combined with deionized water at 60 C to produce 2% solutions. The resulting solutions were combined with an essential oil blend composition (4% alpha-pinene, 30% para-cymene, 7% linalool, and 35% thymol and 24% soybean oil) in a 50:50 weight ratio with deionized water to create an oil-in-water emulsion. The emulsifiers evaluated were Glycosperse S-20 KFG (Lonza; Fairlawn, N.J.), Polyaldo 10-1-O KFG (Lonza; Fairlawn, N.J.), Aldosperse MS-20 KFG (Lonza; Fairlawn, N.J.), Polyaldo 10-2-P KFG (Lonza; Fairlawn, N.J.), Ryoto sugar ester (S-1570, Mitsubishi-Kagaku Food Corp.; Tokyo, Japan), Precept 8120 (Central Soya; Fort Wayne, Ind.) and sodium caseinate (Alanate-180, New Zealand Dairy Board; Wellington, New Zealand). The sucrose ester (S-1570) was identified as the best emulsifier due to the creation of the smallest and most uniformly dispersed oil droplets within the emulsion. The emulsion created with the sucrose ester also showed the greatest stability after 24 hours storage at room temperature.

Example 2: Microencapsulation of a Functional Ingredient Containing Some Esterified Components in a 75% Shellac/25% Zein Matrix 2400.0 g of distilled, ionized water (D.I.H20) was added to a beaker mixed using StedFast Stirrer SL1200 (Yamato Scientific; Tokyo, Japan) with a 4-pronged impeller blade at speed setting between 5 and 6. 37.5 g of Jet Milled zein (F4000, Freeman Industries; Tuckahoe, N.Y.) powder was added to the beaker and mixed until uniformly dispersed. Next, 10% NaOH aqueous solution was added until the pH reached 11.3. The zein-water mixture was agitated until the zein powder was completely dissolved and the solution was translucent. Next, 450.0 g of the pre-made shellac (Temuss #594; Ajax, ON., Canada) in ammonium hydroxide solution (25% solids) was added and mixed for 5-10 minutes. Finally, 1.4 g of sucrose stearate, S-1570 (Mitsubishi-Kagaku Food Corp.; Tokyo, Japan) was added while mixing, such as for 5-10 minutes until homogeneous mixing has occurred.

Next, 80.0 g of the essential oil blend (18.8% canola oil, 8.6% alpha-pinene, 39.8% Para-cymene, 5.4% linalyl acetate and 27.4% thymyl acetate) was added and mixed for 5-10 minutes. Using the PowerGen 700D (Thermo Fisher Scientific; Waltham, Mass.), the mixture was homogenized by blending for 4 minutes at 15,000 rpm, and then at 20,000 rpm for an additional minute to create the stable emulsion. Acid titration of the emulsion using 3% citric acid solution followed using Master Flex pump (Barnant Corp.; Barrington, Ill.) at the highest speed setting with moderate overhead mixing until the pH reached 3.8, thereby creating a slurry.

10 g of SiO2 AB-D (PPG Industries; Pittsburg, Pa.) was added to the slurry and continued to be mixed for 20-30 minutes. The mixture was filtered using a #200 mesh (75 micrometer) screen. In a separate, clean 4000 ml plastic beaker, 2000.0 g of D.I. H20 and add 2.5 g of SiO2 AB-D was mixed to create a solution. The cake was resuspended in this solution and mixed for 3-5 minutes. The mixture was filtered using a #200 mesh screen.

In a separate, clean 4000 ml plastic beaker, 2000.0 g of D.I. H20 and 2.5 g of SiO2 AB-D was mixed to create another solution. The cake was resuspended again and mixed for 3-5 minutes. The filtrate was pressed using cheese cloth to remove the extra moisture. The filtrate was then spread evenly on large tray on top of a cookie sheet for overnight drying, uncovered and at room temperature.

The dried particles were ground using a Magic Bullet MB1001 (Sino Link International Trading Co.; Zhejiang, China). Particles between 75 to 250 micrometers were separated using #60 and #200 mesh sieves. The moisture content was measured using the CEM Smart System 5 (CEM Corp.; Matthews, N.C.). To reduce the moisture content to less than about 6.0 percent, the filtrate was dried in a Uni-Glatt fluid bed dryer (Glatt Air Techniques; Ramsey, N.J.) at 40 C, checking every 5 minutes. As a result, the final product had a moisture content of less than about 6.0 percent. The fraction was sifted by passing through a #60 mesh screen and collected on a #200 mesh screen, thereby producing particles having a size of less than 250 micrometers and greater than 75 micrometers. The composition, payload, and surface oil of the resultant product are illustrated in the table below.

| | alpha-Pinene wt % | para-Cymene wt % | Linalool wt % | Linalyl Acetate wt % | Thymol wt % | Thymyl Acetate wt % | Canola Oil wt % | Total EOS wt % | Total Loading wt % |
|---|---|---|---|---|---|---|---|---|---|
| Total Loading | 0.57 | 1.3 | <0.1 | 1.8 | 0.12 | 9.5 | 5.0 | 13.4 | 18.4 |
| Surface oils | 0.09 | 0.31 | <0.001 | 0.34 | <0.002 | 1.6 | 3.0 | 2.3 | 5.3 |

Example 3: Microencapsulation of a Functional Ingredient Containing Some Esterified Components in 75% Shellac/25% Zein Matrix at a Pilot Plant Scale 12 kg of water and 7.5 g of sucrose stearate (S-1570, Mitsubishi-Kagaku Food Corp.; Tokyo, Japan) was added to a mixing tank and mixed for 1-2 minutes. Then 2.25 kg of pre-made shellac solution (Temuss #594; Ajax, ON., Canada) in ammonium hydroxide solution (25% solids) was added, followed by 187.5 g zein powder (F4000, Freeman Industries; Tuckahoe, N.Y.). 10% sodium hydroxide solution was metered in until pH reached 11.3 (to solubilize zein). Once the zein and shellac are completely in solution, 400 g of essential oil blend (13% canola oil, 10% alpha-pinene, 25% para-cymene, 12% linalyl acetate, and 40% thymyl acetate) was added. The mix was agitated for 5 minutes to create an emulsion.

The emulsion was titrated with 3.0 percent citric acid solution until the pH reached 3.9. 75 g of SiO2 AB-D (PPG Industries; Pittsburg, Pa.) was added and mixed for about 20-30 minutes. The slurry was then filtered using a 200 mesh (75 micrometer) screen. The filter cake on top of the screen was suspended in 9.1 kg of water with 50 g SiO2 AB-D and mixed for approximately 5 minutes, and then refiltered on the #200 mesh screen. The rinsing was repeated one more time, and the final filter cake was spread on a tray for drying overnight at room temperature. The following day, the product was pulverized in a Waring blender (Waring Lab Science; Torrington, Conn.), and dried in a UniGlatt fluid bed (Glatt Air Techniques; Ramsey, N.J.) at 40 C, and sieved to a desired size (75-250 micrometers). The payload and surface oil of the resultant product are illustrated in the table below.

| Sample Description | | Total EOS wt % | Total Loading wt % |
|---|---|---|---|
| Fluid Bed Dried shellac/zein, pilot plant scale w/ ester compounds | Total Loading | 14.3 | 18.8 |
| | Surface oils | 3.8 | 7.2 |

Example 4: Microencapsulation of a Functional Ingredient Containing Some Esterified Components with Increased Oil Loading in a Shellac/Zein Matrix Containing Whey Protein as an Emulsifier 2400.0 g of D.I. H20 was added to a beaker and mixed using StedFast Stirrer SL1200 (Yamato Scientific; Tokyo, Japan) with a 4-pronged impeller blade at speed setting between 5 and 6. 32.5 g of Jet Milled zein powder (F4000, Freeman Industries; Tuckahoe, N.Y.) was added to the beaker and mixed until uniformly dispersed. 10% NaOH solution was added until the pH reached 11.3 and mixed until the zein powder was completely dissolved and the solution was translucent. 20.0 g of BiPro WPI (Davisco Foods International; Eden Prairie, Minn.) powder was next added and mixed until the powder was completely dissolved. Next, 390.0 g of the pre-made shellac solution with 25 percent solids (Temuss #594; Ajax, ON., Canada) containing ammonium hydroxide was added and mixed for 5-10 minutes until the solution was homogeneous.

151.4 g of the essential oil blend (13% canola oil, 10% alpha-pinene, 25% para-cymene, 12% linalyl acetate, and 40% thymyl acetate) was added and mixed for 5-10 minutes. Using the PowerGen 700D (Thermo Fisher Scientific; Waltham, Mass.), the mixture was homogenized for 4 minutes at 15,000 rpm and then at an increased speed of 20,000 rpm for 1 additional minute to create a stable emulsion. 3% citric acid solution was titrated into the emulsion using Master Flex pump until the pH reached 3.8, thereby creating a slurry.

10 g of SiO2 AB-D (PPG Industries; Pittsburg, Pa.) was added to the slurry and mixed for 20-30 minutes. The mixture was filtered using a #200 mesh screen. In a separate, clean 4000 ml plastic beaker, 2000.0 g of D.I. H20 was added and mixed using a StedFast Stirrer. The pH was adjusted to 3.8+/−0.2 by adding 3% citric acid solution. 1 g sucrose stearate, S-1570 (Mitsubishi-Kagaku Food Corp.; Tokyo, Japan) was added and mixed until completely dissolved, followed by an addition of 2.5 g of SiO2 AB-D. The cake was resuspended in this solution and mixed for 3-5 minutes. The mixture was filtered using #200 mesh (75 micrometer) screen. In a separate, clean 4000 ml plastic beaker, 2000.0 g of D.I. H20 was mixed and pH adjusted to 3.8+/−0.2 by adding 3.0 percent citric acid solution. 1 g sucrose stearate was added and mixed until completely dissolved, followed by an addition of 2.5 g of SiO2 AB-D. The cake was resuspended in this solution and mixed for 3-5 minutes. The mixture was filtered again using #200 mesh (75 micrometer) screen.

The resulting filtrate was pressed using cheese cloth to reduce moisture content. The filtrate was spread evenly on a large tray on top of a cookie sheet to dry overnight, uncovered and at room temperature.

The resultant particles were ground using a Magic Bullet MB1001 (Sino Link International Trading Co.; Zhejiang, China). The particles sized less than 250 micrometers were separated from the rest using a #60 mesh screen. To reduce the moisture content to less than about 6.0 percent, the filtrate was dried in a Uni-Glatt fluid bed dryer (Glatt Air Techniques; Ramsey, N.J.) at 40 C, checking every 5 minutes. As a result, the final product had a moisture content of less than about 6.0 percent. The composition, payload, and surface oil of the resultant product are illustrated in the table below.

| | alpha-Pinene wt % | para-Cymene wt % | Linalool wt % | Linalyl Acetate wt % | Thymol wt % | Thymyl Acetate wt % | Canola Oil wt % | Total EOS wt % | Total Loading wt % |
|---|---|---|---|---|---|---|---|---|---|
| Total Loading | 1.12 | 2.7 | <0.10 | 2.7 | <0.10 | 11.3 | 5.7 | 17.9 | 23.5 |
| Surface oils | 0.014 | 0.094 | <0.001 | 0.11 | <0.002 | 0.55 | 2.8 | 0.76 | 3.6 |

Example 5: Microencapsulation of a Functional Ingredient Containing Some Esterified Components in a Matrix Containing 48% Alginate/40% Shellac and 12% Whey Protein as an Emulsifier 2.1 g of sodium alginate (ULV-L3G, Kimica Corp; Tokyo, Japan) and 11.2 g of sodium alginate (I-3G-150, Kimica Corp; Tokyo, Japan) was added to 551.32 g of water. Under agitation, 70 g of a 10% BiPro (Davisco Foods International; Eden Prairie, Minn.) whey protein isolate solution and 56 g of the pre-made shellac (Temuss #594; Ajax, ON., Canada) in ammonium hydroxide solution (25% solids) was added. Next, the essential oil blend (17.41% canola oil, 6.65% alpha-pinene, 26.58% para-cymene, 7.91% linalyl acetate, and 41.46% thymyl acetate) was added and mixed until a homogenous emulsion was formed with target droplet size of 4-7 micrometers, verified with the Horiba particle size analyzer (Horiba Industries; Irvine, Calif.). The solution was then atomized, creating moderately small spheres between 25-300 micrometers, into an aqueous solution bath containing 2.5% CaCl2 and 2.5% citric acid. The spheres were placed on a 25 micrometer screen to remove the bath solution, after which they were dried at 40 C in the MiniGlatt fluidized bed dryer (Glatt Air Techniques; Ramsey, N.J.) until the target moisture (5-6%) was reached. The particles were sized to less than 500 micrometers and greater than 75 micrometers. The composition, payload, and surface oil of the resultant product are illustrated in the table below.

|  | alpha-Pinene wt % | para-Cymene wt % | Linalool wt % | Linalyl Acetate wt % | Thymol wt % | Thymyl Acetate wt % | Canola Oil wt % | Total EOS wt % | Total Loading wt % |
|---|---|---|---|---|---|---|---|---|---|
| Total Loading | 1.96 | 7.5 | na | 2.6 | na | 14.6 | 7.0 | 26.70 | 33.71 |
| Surface oils | 0.002 | 0.007 | 0.002 | 0.004 | <0.002 | 0.063 | 0.58 | 0.076 | 0.654 |

Example 6: Non-Esterified Functional Ingredient Microencapsulated in an Alginate/Shellac Matrix 48.0 g of sodium alginate (ULV-L3G, Kimica Corp; Tokyo, Japan) and 10.0 g of sodium alginate (I-3G-150, Kimica Corp; Tokyo, Japan) was added to 840.0 g of water. Then, under agitated conditions, 80 g of the pre-made shellac solution w/25% solids (Marcoat 125, Emerson Resources; Norristown, Pa.) was added. Next, 48 g of the essential oil blend (24% soybean oil, 4% alpha-pinene, 30% para-cymene, 7% linalool, and 35% thymol) was added and mixed and homogenized until a fine, stable emulsion was formed. Using a two-fluid nozzle, the solution was atomized, creating moderately small spheres of 25-300 micrometers, into an aqueous hardening bath containing 2.5% CaCl2 and 2.5% citric acid. After the particles were cross-linked, the particles were sieved on a 25 micrometer sieve and dried at 40 C in the MiniGlatt fluid bed dryer (Glatt Air Techniques; Ramsey, N.J.) until the target moisture (5-6%) was reached. Particles were sized at less than 212 micrometers.

As seen in the table below, the payload was low and the particles failed to mask the undesirable taste/flavor of the essential oil when tasted in a model beverage system. The composition and payload of the resultant product are illustrated in the table below.

|  | alpha-Pinene wt % | para-Cymene wt % | Linalool wt % | Thymol wt % | Soybean Oil wt % | Total EOS wt % | Total Loading wt % |
|---|---|---|---|---|---|---|---|
| Total Loading | <.01 | 2.8 | .031 | 1.7 | 4.8 | 4.5 | 9.3 |

Example 7: Microencapsulation of an Essential Oil Blend Containing Some Esterified Components in a 75% Alginate/25% Shellac Matrix 5.5 g of sodium alginate (ULV-L3G, Kimica Corp; Tokyo, Japan) and 11.0 g of sodium alginate (I-3G-150, Kimica Corp; Tokyo, Japan) was added to 495 g of water. Then, under agitation, 22.0 g of the pre-made shellac (Temuss #594; Ajax, ON., Canada) in ammonium hydroxide solution (25% solids) was added. Next, the essential oil blend (18.50% canola oil, 5.48% alpha-pinene, 32.39% para-cymene, 11.26% butyric acid ester of linalool (linalyl butyrate) and 32.37% acetic acid ester of thymol (thymyl acetate)) was added and mixed and homogenized until a fine, stable emulsion was formed with target droplet size of 4-7 micrometers, verified with the Horiba particle size analyzer (Horiba Industries; Irvine, Calif.). The solution was atomized, creating moderately small spheres between 25-300 micrometers, into an aqueous hardening bath containing 2.5% Cacl2 and 2.5% citric acid. The particles were then sieved on a 25 micrometer screen to remove the bath solution and then dried at 40 C in the MiniGlatt fluidized bed dryer (Glatt Air Techniques; Ramsey, N.J.) until the target moisture (5-6%) was reached. The particles were sized to less than 212 micrometers.

As shown in the table below and compared to Example 6, payload was increased significantly upon using a functional ingredient containing esterified components. In particular, as can be seen in FIG. 2, an unexpected benefit of using an esterified component is that the payload of the non-esterified components also increased in the presence of esterified component. Further, the esterified components produced a less negative flavor/taste impact than the product formed in Example 6. The composition, payload, and surface oil of the resultant product are illustrated in the table below.

|  | alpha-Pinene wt % | para-Cymene wt % | Linalool wt % | Linalyl Butyrate wt % | Thymol wt % | Thymyl Acetate wt % | Canola Oil wt % | Total EOS wt % | Total Loading wt % |
|---|---|---|---|---|---|---|---|---|---|
| Total Loading | 1.80 | 9.2 | na | 3.9 | na | 10.8 | 8.0 | 25.70 | 33.70 |
| Surface oils | 0.002 | 0.019 | na | 0.006 | na | 0.066 | 0.61 | 0.093 | 0.701 |

Example 8: Comparison of Payload Retention with Non-Esterified and Esterified Functional Ingredients within a 75% Alginate/25% Shellac Matrix Comparison of the particles produced with the original essential oil blend (containing non-esterified components: alpha-pinene, para-cymene, linalool, thymol, and canola oil) and particles produced with an essential oil blend containing some esterified components (alpha-pinene, para-cymene, linalyl butyrate, thymyl acetate, and canola oil) is illustrated in FIG. 2. The particles were produced using the same process conditions and compositions aside from the esterified versus non-esterified functional ingredients. In this figure, the level of linalool (combined) is calculated by summing the measured linalool and the linalool equivalent from the measured linalyl acetate based on the molecular composition.

As shown in FIG. 2, it is evident that the use of some esterified components in the essential oil blend led to about a 130% increase in microencapsulation efficiency, the microencapsulation efficiency increase seen in both the esterified and non-esterified components of the functional ingredient.

Example 9: Effect of an Esterified Functional Ingredient on Gastric Release

This example compares the release of the non-esterified functional ingredient to the esterified functional ingredient during a simulated gastrointestinal study using an in vitro digestion model.

Figure 4:
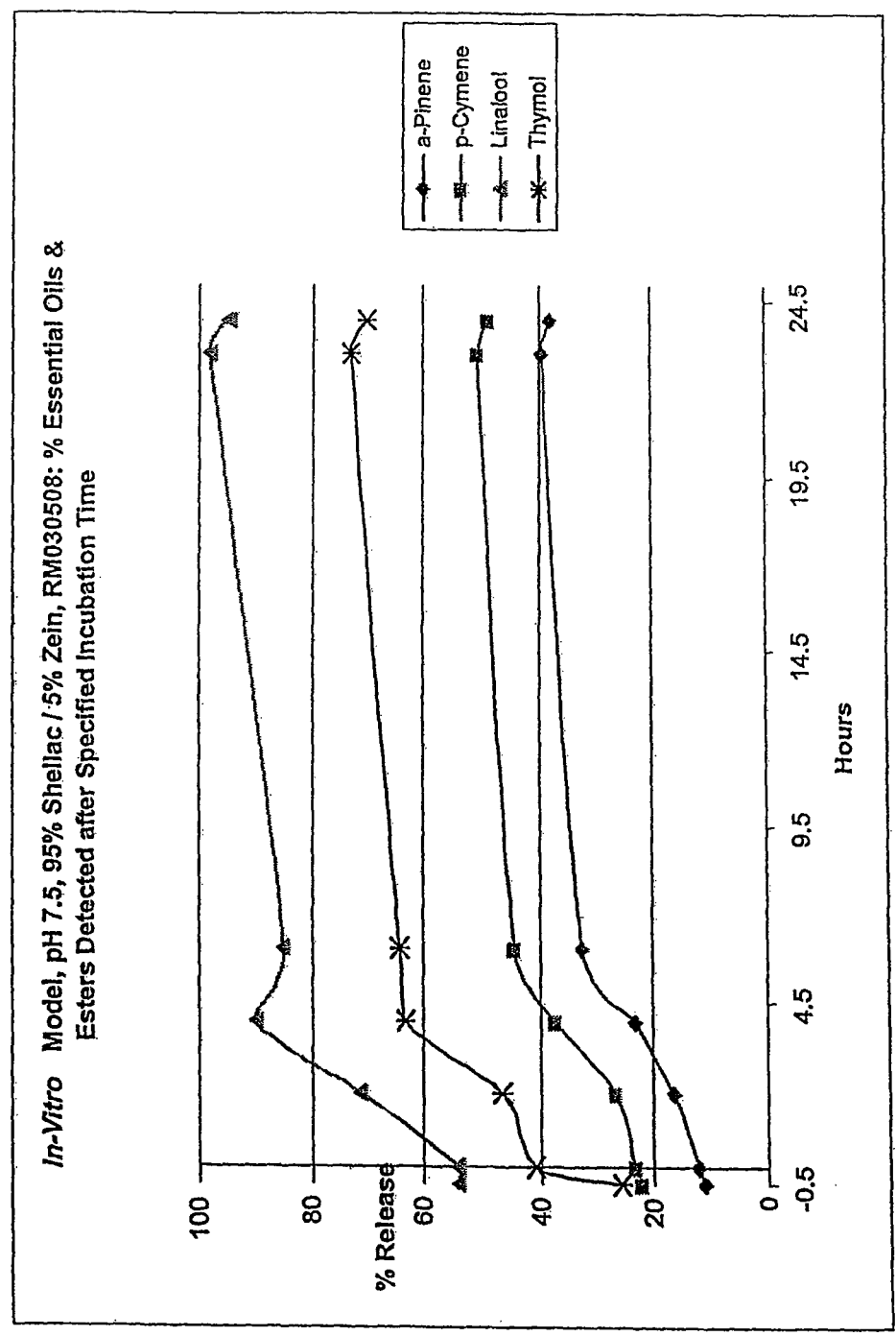
FIG. 4 is a chart illustrating the release rates of the various components of a functional ingredient which does not include esters with an enteric matrix comprised of 95 percent shellac and 5 percent zein.
Figure 5:
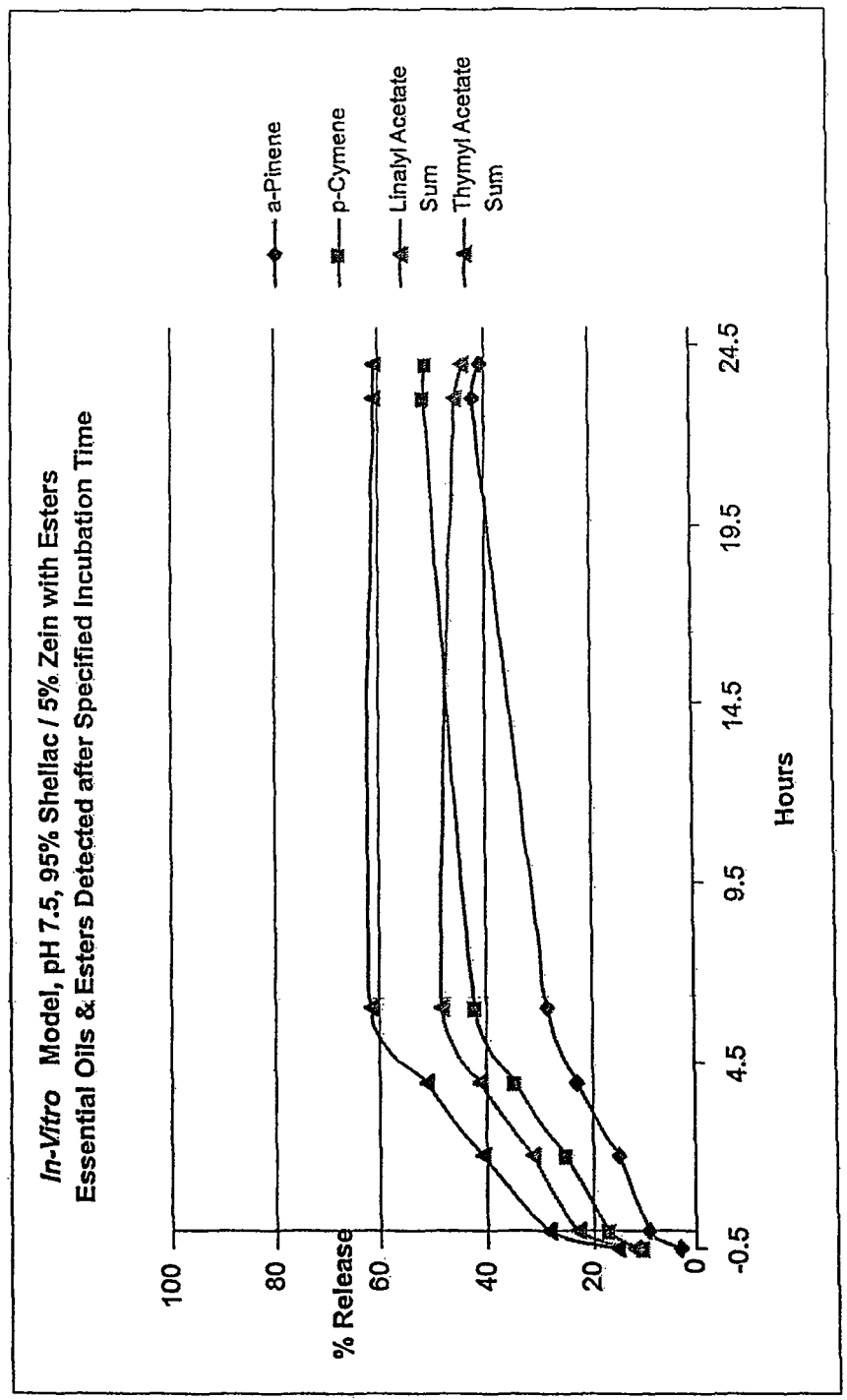
FIG. 5 is a chart illustrating the release rates of the various components of a functional ingredient including esters with an enteric matrix comprised of 95 percent shellac and 5 percent zein.

FIG. 3 shows the known properties of the compounds. As shown in FIG. 3, the solubility values for the ester compounds (linalyl acetate, linalyl butyrate and thymyl acetate) are significantly lower than the parent compounds (linalool and thymol). In addition, the partition coefficients for the ester compounds are greater than the parent compounds. These factors indicate that the ester compounds have a greater affinity for the hydrophobic carrier and insoluble matrix material than the parent compounds. FIGS. 4 and 5 show that the release between −0.5 and 0.0 hours, representative of the residence time in the simulated gastric fluid, is greatly reduced for the particles containing some esterified functional ingredient. The reduced rate is most evident when comparing linalool and thymol release from FIG. 4 to linalyl acetate and thymyl acetate release from FIG. 5. This improvement in stability within the model stomach implies increased stability in other low pH systems, such as acidic beverages, and further illustrates the importance of the esters for successful microencapsulation and enteric release of the functional ingredients.

Figure 6:
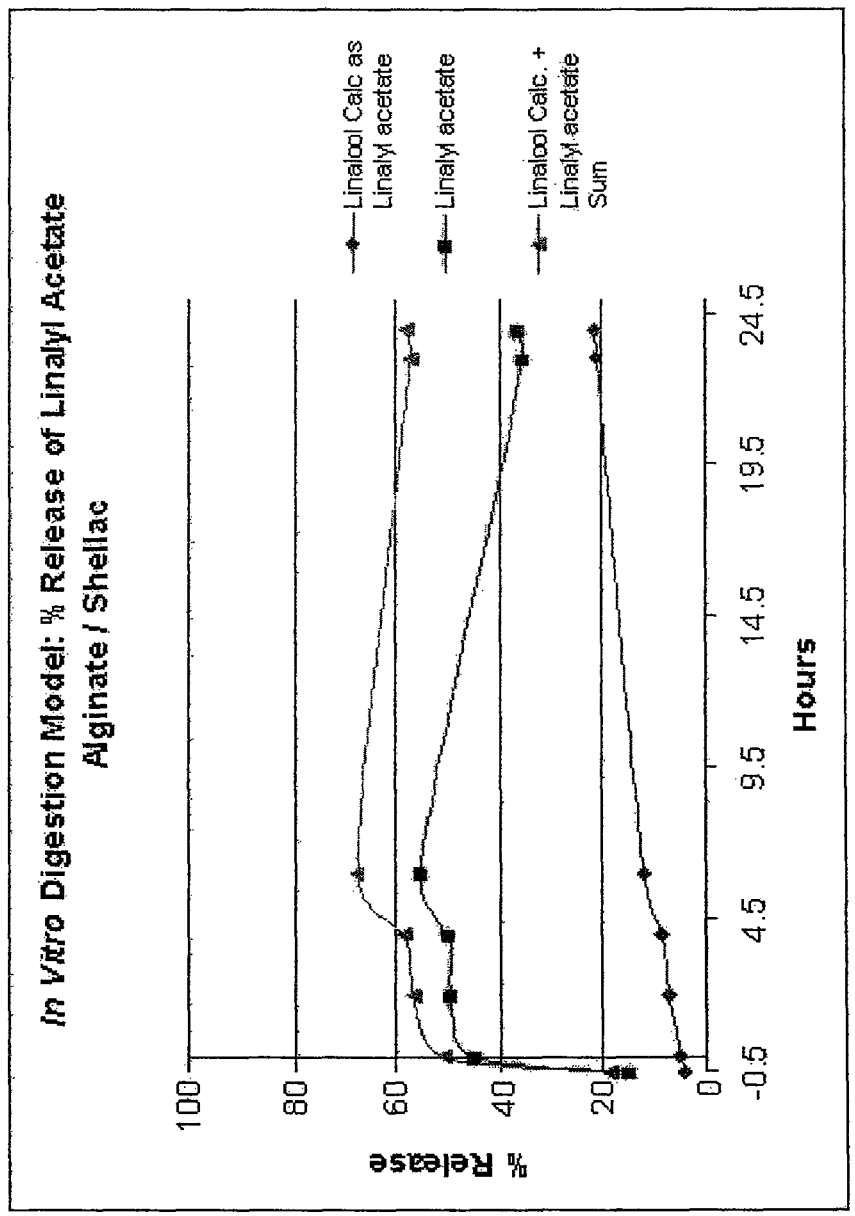
FIG. 6 is a chart illustrating the release rates of the various components of a functional ingredient comprising linalyl acetate within a digestion model simulating stomach and small intestine conditions.
Figure 7:
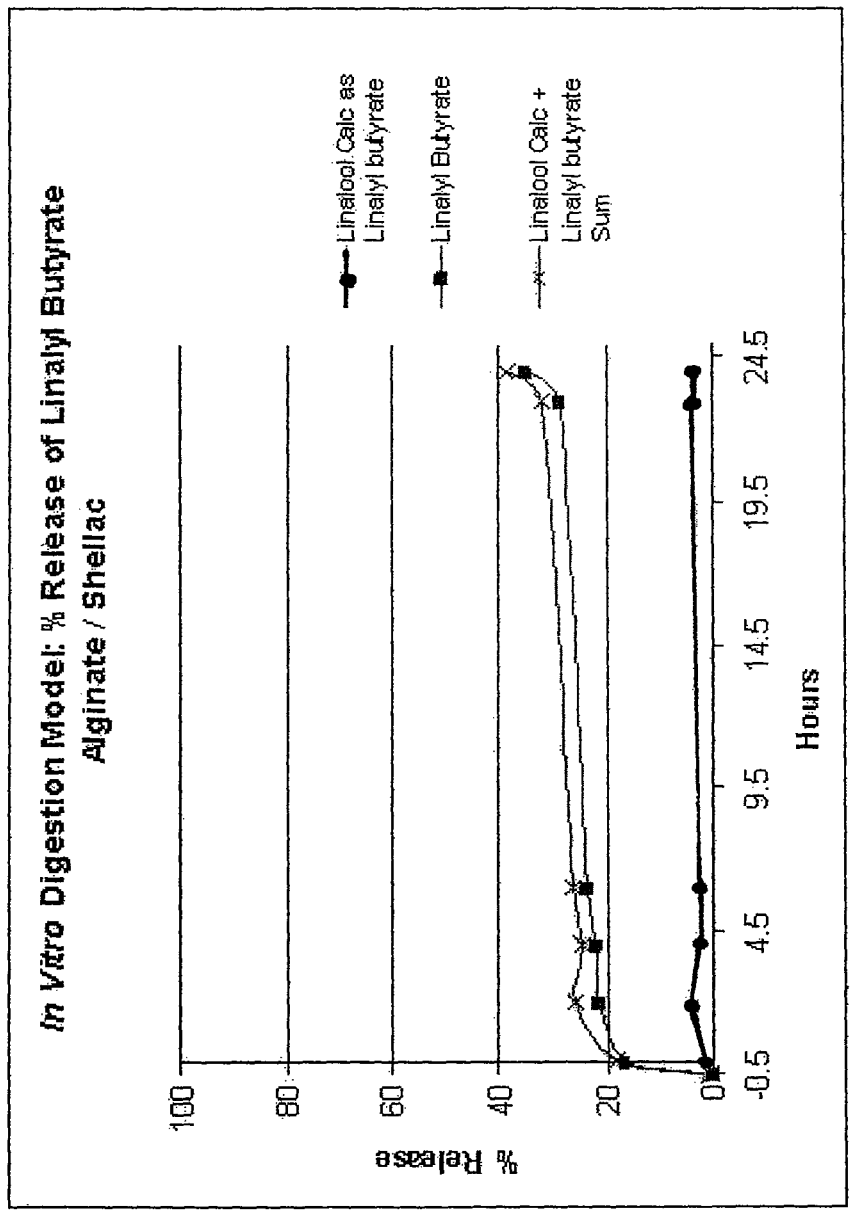
FIG. 7 is a chart illustrating the release rates of the various components of a functional ingredient comprising linalyl butyrate within a digestion model simulating stomach and small intestine conditions.

Example 10: Modulation of the Release from Microencapsulated Particles and the Hydrolysis of the Esterified Components This example shows how the selection of various acids for esterification can affect the resulting rate of delivery of the parent compounds. Example 9 showed the effect on release rate from the particles within a gastric model, as a result of inclusion of some esterified compounds. As evident in FIGS. 4 and 5, the gastric release rate was reduced, as well as the release rate from 0-24.5 h, representative of the residence time in the small intestine. FIGS. 6 and 7 show the release rates of two esters of linalool, linalyl acetate in FIG. 6 and linalyl butyrate in FIG. 7 within a digestion model simulating stomach and small intestine conditions and residence times. In addition, the levels of the parent compounds present in the digestion model over time were measured. The presence of the parent compound, linalool is a result of hydrolysis of the linalyl acetate. As seen in FIG. 6, the initial release of linalool was about 5% and increases to about 20%, which correlates to about 33% hydrolysis of linalyl acetate to linalool. In FIG. 7, the initial release of linalool was about 2% and increases to about 4%, which correlated to about 5% hydrolysis of the linalyl butyrate to linalool. From those results, it can be seen that by formulating the functional ingredient with varying ratios of linalyl acetate to linalyl butyrate, the resulting level of linalool release through the gastric tract and small intestine can be modulated.

Example 11: Comparison of Model Beverage Systems with Esterified and Non-Esterified Functional Ingredient The taste profiles of two model beverages were informally compared. One beverage was prepared with particles comprising non-esterified functional ingredient with the other beverage was prepared with particles comprising some esterified functional ingredient, namely linalyl and thymyl acetates. Particles were created in the same manner as Example 2. Two equal, one-serving amounts of powdered beverage mix were portioned out. To the first portion, a sufficient mass of the particles comprising the non-esterified functional ingredient was added so that 70 mg of the functional ingredient was dosed. To the second portion, a sufficient mass of the particles comprising some esterified functional ingredient was added so that 70 mg of the functional ingredient was dosed. Each powder/particle mixture was then added to 200 ml of cold water and mixed thoroughly.

Upon tasting samples of each model beverage, the panel concluded that the model beverage containing particles comprised of some esterified functional ingredient had a significantly reduced undesirable taste and/or flavor profile, leading to an improved overall sensory experience.

While the invention has been particularly described with specific reference to particular process and product embodiments, it will be appreciated that various alterations, modifications, and adaptations may be based on the present disclosure, and are intended to be within the spirit and scope of the invention as defined by the following claims.

What is claimed is:

1. A composition comprising:
    a functional ingredient;
    a non-active carrier; and
    an enteric matrix microencapsulating the functional ingredient and non-active carrier and comprising a food grade enteric polymer,
    wherein the functional ingredient comprises at least about 10% esterified essential oils that are configured to hydrolyze into parent, non-esterified essential oils and at least one non-esterified functional component, wherein the esterified essential oils have a microencapsulation efficiency that is at least about 50% greater than the microencapsulation efficiency of the parent, non-esterified essential oils and the non-esterified functional component has an increased microencapsulation efficiency than when in a comparable enteric matrix, wherein the esterified essential oils comprise esters of thymol.

2. The composition of claim 1 wherein the esterified essential oils comprise esters of linalool and thymol.

3. The composition of claim 2 wherein the ratio of thymyl ester to linalyl ester ranges from about 2:1 to about 6:1.

4. The composition of claim 1 wherein the functional ingredient comprises at least about 20% esterified essential oils that are configured to hydrolyze into parent, non-esterified essential oils.

5. The composition of claim 4 wherein the functional ingredient comprises at least about 50% esterified essential oils that are configured to hydrolyze into parent, non-esterified essential oils.

6. The composition of claim 1 wherein the functional ingredient further comprises alpha-pinene and para-cymene.

7. The composition of claim 1 wherein the non-active carrier comprises a lipid.

8. The composition of claim 7 wherein the lipid is a triglyceride.

9. The composition of claim 8 wherein the triglyceride is selected from the group including soybean oil and canola oil.

10. The composition of claim 1 wherein the ratio of functional ingredient to enteric matrix material ranges from about 1:19 to about 1:1.

11. The composition of claim 1 wherein the microencapsulated functional ingredient and non-active carrier comprises a particulate.

12. The composition of claim 11 wherein the particulate has a moisture content of less than about 6.0 percent.

13. The composition of claim 11 wherein the particulate has a particle size of less than about 1,000.0 micrometers.

14. The composition of claim 1 wherein the enteric matrix is selected from the group consisting of zein, shellac, calcium alginate and mixtures thereof.

15. The composition of claim 1 having a payload ranging from about 5.0 to about 50.0 percent.

16. The composition of claim 1 including less than about 1.0 percent by weight unencapsulated material.

17. A composition comprising:
    a functional ingredient comprising at least about 10% esterified essential oils and at least one non-esterified functional component, wherein the esterified essential oils comprise esters of thymol;
    a non-active carrier; and
    an enteric matrix microencapsulating the functional ingredient and non-active carrier, the enteric matrix comprising at least one of shellac, zein and mixtures thereof configured to resist digestion in the stomach such that the enteric matrix remains substantially intact until it enters the small intestine where the esterified essential oils are released to hydrolyze into parent, non-esterified essential oils,
    wherein the esterified essential oils have a microencapsulation efficiency that is at least about 50% greater than the microencapsulation efficiency of the parent, non-esterified essential oils and the non-esterified functional component has an increased microencapsulation efficiency than when in a comparable enteric matrix.

18. The composition of claim 17 wherein the esterified essential oils have at least about 100% increase in payload retention in the enteric matrix compared to non-esterified essential oils free of esterified essential oils in a comparable enteric matrix.

* * * * *